United States Patent [19]

Adahan

[11] Patent Number: 4,941,469
[45] Date of Patent: Jul. 17, 1990

[54] PORTABLE VENTILATOR APPARATUS

[76] Inventor: Carmeli Adahan, 1316/02 Ramot 03, Jerusalem 97 725, Israel

[21] Appl. No.: 197,198

[22] Filed: May 23, 1988

Related U.S. Application Data

[63] Continuation-in-part of Ser. No. 119,880, Nov. 12, 1987, Pat. No. 4,807,616, which is a continuation-in-part of Ser. No. 71,327, Jul. 9, 1987, Pat. No. 4,823,787.

[51] Int. Cl.$^5$ .................. A61M 16/16; A61M 16/10
[52] U.S. Cl. .................. 128/205.18; 128/205.11; 128/205.24; 128/203.12; 128/203.16
[58] Field of Search .................. 128/204.21, 205.18, 128/204.18, 205.11, 205.19, 204.26, 203.12, 203.16, 205.24; 417/542

[56] References Cited

U.S. PATENT DOCUMENTS

| | | | |
|---|---|---|---|
| 2,951,450 | 9/1960 | Fisher | 417/542 |
| 3,658,443 | 4/1972 | Fumigalli | 128/204.18 |
| 3,682,166 | 8/1972 | Jacobs | 128/205.19 |
| 3,766,914 | 10/1973 | Jacobs | 128/205.19 |
| 3,842,828 | 10/1974 | Bird | 128/202.22 |
| 4,096,858 | 6/1978 | Eyrick et al. | 128/204.21 |
| 4,471,773 | 9/1984 | Bunnell et al. | 128/204.21 |
| 4,508,117 | 4/1985 | Rodari | 128/204.21 |
| 4,527,557 | 7/1985 | DeVries et al. | 128/204.23 |
| 4,611,591 | 9/1986 | Inui et al. | 128/204.21 |

Primary Examiner—Edgar S. Burr
Assistant Examiner—Kimberly L. Asher
Attorney, Agent, or Firm—Benjamin J. Barish

[57] ABSTRACT

Ventilator apparatus comprises a cyclically-operated reciprocating pump, a delivery tube for delivering pressurized air to a patient, an exhalation valve assembly producing breathing cycles in which the delivery tube is first connected to the patient to effect inhalation and then is vented to the atmosphere to permit exhalation, and a control valve operated by the pump for controlling the breathing cycles of the exhalation valve. The pump has a low volume-displacement and operates at a relatively high cyclical speed, thereby enabling the apparatus to be selectively operated to perform the functions of any one of a large number of different types of ventilators.

20 Claims, 2 Drawing Sheets

PORTABLE VENTILATOR APPARATUS

RELATED APPLICATIONS

This application is a continuation-in-part of my U.S. patent application Ser. No. 07/119,880 filed Nov. 12, 1987, now U.S. Pat. No. 4,807,616, which in turn is a continuation-in-part of my U.S. patent application Ser. No. 07/071,327, filed July 9, 1987, now U.S. Pat. No. 4,823,787 and is particularly directed to an improved ventilator apparatus described in those patent applications.

BACKGROUND OF THE INVENTION

The present invention relates to ventilator apparatus, and particularly to portable ventilator apparatus useful for providing mechanical ventilation of a patient at home or during transport.

Ventilating apparatus is widely used for mechanically forcing air into the lungs of a patient requiring ventilatory assistance. Some ventilators are designed for continuous use in hospitals, such as in intensive care units; and others are designed as portable units for use in the home or during transport. Examples of the latter are described in U.S. Pat. Nos. 3,499,601, 4,215,681 and 4,493,614. The present invention is particularly applicable to ventilators of the portable type for use in the home or during transport.

Ventilators are usually also divided into the following types:

1. Pressure ventilators, usually including a source of compressed air administered by a solenoid valve at a rate of one cycle per breath, 10–30 breaths per minute.

2. Volume ventilators, usually including a large reciprocating piston driven by an electric motor for compressing air into the patient's lungs at a preset fixed volume with the cycling frequency of one cycle per breath, 5 to 40 breaths per minute.

Both of the above type ventilators usually include large-size pistons (e.g., 10–12 inch diameters) having sealing surfaces with respect to the cylinders in which they move, and in general are characterized by bulky construction precluding portability, high power consumption because of continuous operation precluding the use of batteries, and/or poor control of the volume the patient inhales with each breath. Such ventilators are also generally characterized by inability to attain high frequencies required for baby respiration, poor control of the volumes when they are set very low since the piston stroke becomes very critical, and/or poor mechanical efficiency since most of the energy is expended in overcoming friction in the piston seal and in the transmission from the motor to the piston.

3. Continuous positive airway pressure (CPAP) ventilators, usually including a compressor providing continuous positive pressure at a low pressure level. Such ventilators are commonly used only for applying a positive pressure to the patient's lungs in order to help alleviate obstructive apnea during sleep while the patient breathes against the continuous pressure. The presently used CPAP ventilators generally include small turbines, such as vacuum cleaner turbines, generating high air flow rates with low pressure, and a relief valve, commonly called a "PEEP" (Positive End Expiratory Pressure) valve, which releases the pressure to the atmosphere when the pressure in the delivery conduit rises above a predetermined value. However, such known CPAP ventilators are usually not only noisy but also wasteful of power, oxygen and moisture since they generate air flow far in excess of the patient's needs and while the patient is exhaling.

4. High-frequency positive-pressure ventilators, in which a source of compressed air is controlled to deliver air to the patient at controlled volumes and at rates between 60 and 120 breaths per minute. Such ventilators are usually of bulky construction and therefore are primarily used in clinical applications.

5. High-frequency jet ventilators, which include compressors delivering high pressure air directly to the lungs at frequencies of up to 400 cycles per minute.

An object of the present invention is to provide a novel ventilator apparatus which may be embodied in a compact, portable construction, and which may be selectively operated to perform the functions of any one of the above type ventilators.

BRIEF SUMMARY OF THE INVENTION

According to one aspect of the present invention, there is provided ventilator apparatus comprising: a pump including a negative-pressure chamber having an inlet for drawing air into the chamber, and a positive-pressure chamber having an outlet for outletting pressurized air; delivery means for delivering pressurized air to a patient; an exhalation valve assembly producing breathing cycles in which the delivery means is first connected to the patient to effect inhalation, and then is vented to the atmosphere to permit exhalation; and a control valve operated by the pump for controlling the breathing cycles of the exhalation valve; characterized in that the pump is a cyclically-operated reciprocating pump is a cyclically-operated reciprocating pump and has a low volume-displacement, operates at a cyclical speed to effect at least 2 cycles of operation for each breathing cycle of the exhalation valve, and includes an expansible member in the flow path of the air from the positive pressure chamber to the delivery means to damp oscillations produced by the reciprocating pump.

In the described preferred embodiment, the low volume displacement pump includes two pistons reciprocated within a cylinder, each of the pistons having a diameter of less than 40 mm, preferably about 32 mm (1.25 inch), and is operated at about 20–30 cycles per breath. A pump having this order of displacement is considered to be a low volume-displacement pump, as distinguished from that commonly used in the present portable ventilators, operated at a speed of one cycle per breath, and having a piston diameter of 250–280 mm (10–12 inches). The novel construction, using a low volume-displacement pump operated at a high cyclical speed (each cycle of operation including a suction stroke and a pressure stroke), as distinguished from the large volume-displacement pumps operated at a relative low cyclical speed in existing ventilators, and including an expansible member, enables the ventilator of the present application to be selectively operated to perform the different functions of the many different types of existing ventilators as described above. The novel construction also more accurately meters the quantity of air supplied, and even obviates the need for seals between the pistons and the cylinder.

According to another feature, the ventilator apparatus further includes an air inlet into the negative-pressure chamber, an oxygen inlet into the negative-pressure chamber, and proportioning means controlling the proportion of the air and oxygen inletted via their respective inlets.

According to a still further feature, the ventilator apparatus further includes a relief valve communicating with the delivery means for preventing the pressure in the delivery means from rising above a predetermined peak; a sensor for sensing the pressure in the delivery means; and control means effective to energize the pump when the sensed pressure in the delivery means is below the peak value, and to deenergize the pump when the sensed pressure is substantially equal to the peak value.

The latter feature makes the novel ventilator apparatus particularly useful as a CPAP ventilator for alleviating obstructive apnea during sleep. In this application, the relief (i.e., the PEEP) valve would be set at a predetermined peak pressure, and the sensor and its control systems (i.e., the storage device and the comparator circuit in the described preferred embodiment) would be effective to intermittently operate the pump so as to avoid wasting power, as well as oxygen and moisture when oxygen and moisture are supplied with the pressurized air to the patient. This makes the CPAP ventilator very efficient and quiet, and enables it to save oxygen and moisture, as well as electrical power. Also, the electrical sensing circuit senses the PEEP pressure upon each exhalation cycle, and memorizes it so that it controls the pump according to that pressure, thereby eliminating the need for any adjustment on behalf of the user.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Overall Construction

Figure 1:
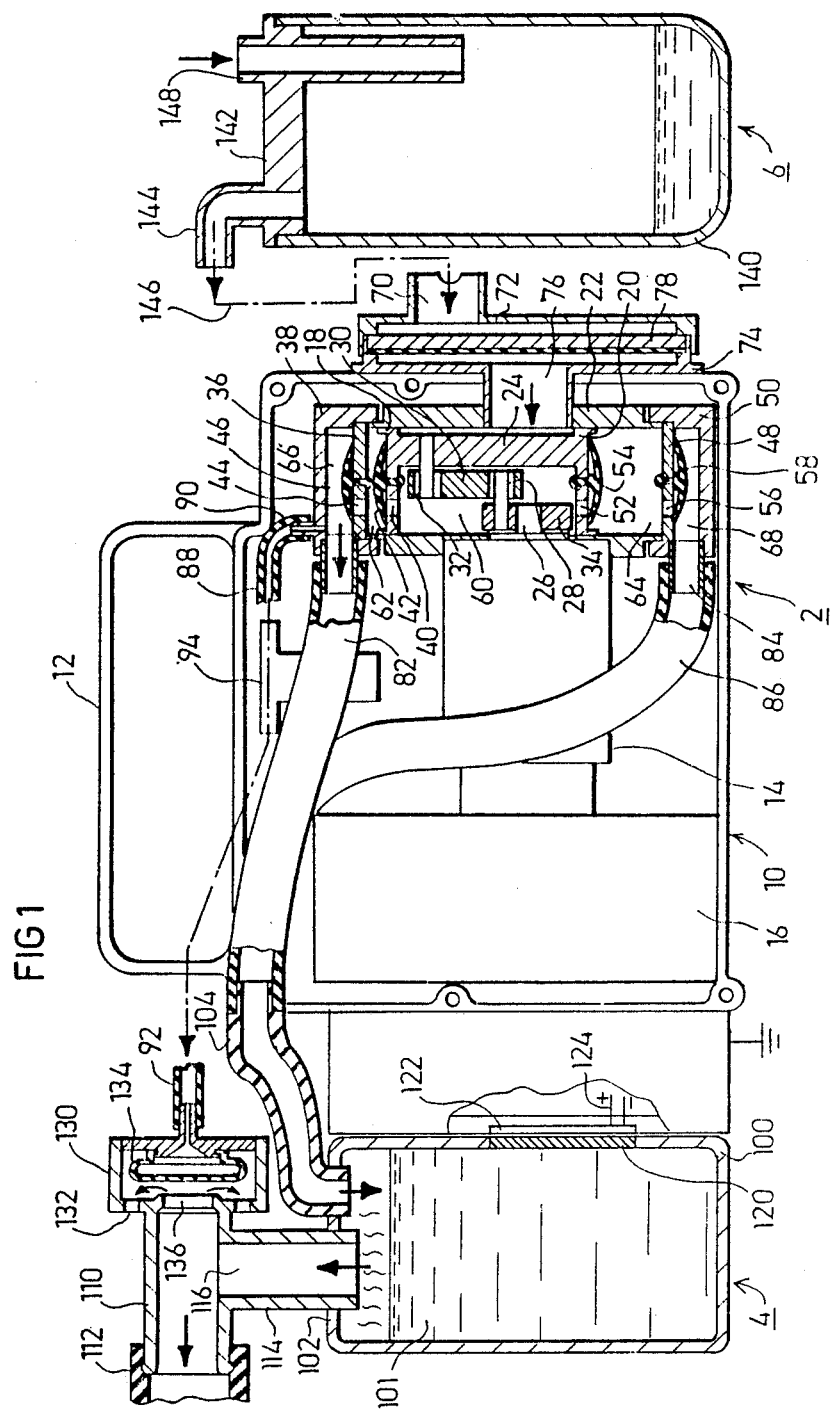
FIG. 1 is a longitudinal section view illustrating one form of ventilator apparatus constructed in accordance with the present invention.

The ventilator apparatus illustrated in FIG. 1 is designed to provide maximum portability. For this purpose, it is constituted of three separate units, namely a pump unit 2, a humidifier unit 4, and a fluid collector unit 6, which may be conveniently detached from each other for transportation or storage, and quickly attached to each other when the apparatus is to be used for providing mechanical ventilation.

Generally speaking, pump unit 2 includes the drive for producing the positive air pressure providing the mechanical ventilation; humidifier unit 4 is connectable to the positive-pressure outlet of the pump unit for humidifying the air outputted by that unit; and fluid collector unit 6 is connectable to the negative-pressure inlet of the pump unit, whenever desired, in order to draw fluid accumulating in the lungs of the patient. Each of these units will be described more particularly below.

Pump Unit 2

Pump unit 2 includes a housing 10 provided with a handle 12 for portability, an electric motor 14 for driving the pump, and a compartment 16 for a self-contained power supply. Motor 14 drives a pair of pistons 18, 20 disposed within a cylinder 22 and connected together by a piston rod 24. Motor 14 is a rotory motor and its output rotary shaft 26 is coupled to piston rod 24 via an eccentric bearing 28, a crank arm 30, and another eccentric bearing 32, so that the rotary output of the motor is converted to a reciprocatory movement of the two pistons 18, 20 within the cylinder 22. The rotary shaft 26 of the motor further includes a flywheel 34.

The end of cylinder 22 adjacent to piston 18 is closed by an end wall 36 fixed to the cylinder by an end fitting 38. Piston 18 is formed with a port 40 closed by an umbrella-type valve 42 disposed on the outer face of the piston to permit air to flow outwardly through port 40 but not in the reverse direction. End wall 36 is similarly formed with a port 44 closed by another umbrella-type valve 46 on the outer face of the end wall to permit air to flow outwardly through port 44 and not in the reverse direction. A similar construction is provided at the opposite end of cylinder 22 adjacent to piston 20, namely an end wall 48 fixed by an end fitting 50, a port 52 through piston 20 closed by an umbrella-type valve 54 on the outer face of the piston, and a port 56 through end wall 48 and closed by an umbrella-type valve 58 on the outer face of the end wall.

It will thus be seen that the space on the inner sides of the two pistons 18, 20 defines a common chamber 60 in which a negative pressure is produced during the reciprocation of the two pistons, and that the spaces on the outer sides of the two pistons define two chambers 62, 64 in which a positive pressure is produced during the reciprocation of the pistons. It will also be seen that the spaces 66 and 68 between the end walls 36 and 48 and their respective end fittings 38 and 50 define two further positive-pressure chambers communicating with the positive-pressure chambers 62 and 64, respectively, through ports 44 and 56 of their respective end walls.

The air drawn into the negative-pressure chamber 60 during the reciprocation of the pistons 18, 20 enters the chamber via an inlet 70 formed in an inlet fitting 72. The latter fitting is removably attached to an annular flange 74 formed in housing 10 around an inlet port 76 communicating with the negative-pressure chamber 60. A filter 78 is interposed between fitting 72 and flange 74 to filter the air inletted into the negative- pressure chamber 60.

The positive-pressure chamber 66 at the piston 18 end of the cylinder 22 includes an outlet fitting adapted to receive a tube 82 for outletting the positive-pressure air produced at that end of the pump; and positive-pressure chamber 68 at the opposite end of the cylinder similarly includes an outlet fitting 84 receiving a tube 86 for outletting the positive-pressure air produced at that end of the pump. The positive-pressure air produced in chamber 66 is further outputted, via a tube 88 secured to a nipple 90 formed in end fitting 38, to another tube 92 for control purposes. The positive-pressure air outputted via tubes 88 and 92 is controlled by a solenoid valve 94, for control purposes as to be described more particularly below.

Humidifier Unit 4

The humidifier unit 4 is in the form of a container 100 for receiving a supply of water 101 to humidify the positive-pressure air outputted by pump unit 2. The upper end of container 100 is closed by a top wall 102 having an inlet T-fitting 104 attachable to the two tubes 82, 86 outletting the positive-pressure air from the two output ends of the pump unit 2.

The humidifier unit 4 further includes an outlet fitting 110, attachable to the top wall 102 of container 100, for receiving a delivery tube 112 to deliver the humidified air to the patient. Delivery tube 112, which may be of any known construction, generally includes a mask (not shown) attachable over the mouth of the patient to receive the mechanical ventilation provided by the illustrated apparatus. Outlet fitting 110 is formed with a connector 114 receivable within an output port 116 formed in the top wall 102 of the humidifier container 100.

Container 100 of the humidifier unit 4 is formed with a metal insert 120 at the side adjacent to the pump unit 2. An insulated electrical heating element 122 is attached to metal insert 120 and is supplied by electrical current via connector 124 of the pump unit 2. The water 101 within container 100 is thus heated by the heat generated by electrical heater 122, as well as by the heat generated within the pump unit 2, to produce vapour which humidifies the air supplied by the pump unit.

Outlet fitting 110 further includes an exhalation valve assembly, generally designated 130, for controlling the exhalation of the patient. Thus, the exhalation valve assembly 130 includes two venting ports 132 for venting the delivery tube 112 to the atmosphere, and a valve member 134, in the form of a mushroom valve, movable either to an open position (shown in FIG. 1) or to a closed position with respect to a valve opening 136 formed in assembly 130.

Mushroom valve 134 is controlled by the pressure applied thereto from the positive-pressure chamber 66 via solenoid valve 94 and tube 92. Normally, mushroom valve 134 is in its open position as illustrated in FIG. 1, thereby establishing communication between delivery tube 112 and venting ports 132, to permit exhalation by the patient to the atmosphere via the latter venting ports; however, when a positive pressure is transmitted to the exhalation valve assembly 130 via tube 92, under the control of solenoid valve 94, mushroom valve 134 moves to its closed position with respect to valve opening 136. This blocks communication between delivery tube 112 and the venting ports 132, and thereby effects inhalation into the patient's lungs by the positive pressure of the air passing through tubes 82, 86, humidifier 100, and delivery tube 112.

Fluid Collection Unit 6

The fluid collector unit 6 is attachable to the negative-pressure inlet connector 70 of the pump unit 2 whenever it is desired to withdraw fluids accumulating in the lungs of the patient. Thus, collector unit 6 includes a container 140 closed at its upper end by a top wall 142 formed with a fitting 144 connectable by a tube, shown schematically at 146, to the negative-pressure inlet 70 of pump unit 2, and with a further coupling 148 adapted to receive another tube, e.g., a catheter tube insertable into the lungs of the patient. Thus, when the fluid collector unit 6 is connected to the negative-pressure inlet 70 of the pump unit 2, the negative pressure produced by the pump unit draws out of the patient's lungs any fluid therein, which fluid is accumulated in container 140.

Overall Use and Operation

Normally the humidifier unit 4 and the fluid collector unit 6 may be detached from the pump unit 2 so as to permit, convenient portability and storage of the apparatus.

When the apparatus is to be used for providing mechanical ventilation of a patient, the humidifier unit 4 is attached to the pump unit 2, and the electric motor 14 is energized to produce positive-pressure air passing through the two outlet tubes 82, 86, via the humidifier unit 4, to the delivery tube 112 attached to the patient. The operation of motor 14 reciprocates the two pistons 18, 20 within cylinder 22, to pump the air from the positive-pressure chambers 62, 66 and 64, 68 at the opposite ends of cylinder 22, via their respective tubes 82, 86 into the humidifier unit 100, where the air is humidified by the water heated by the electrical heating element 120 before passing to the delivery tube 112.

The positive-pressure air thus applied to the delivery tube 112 is controlled by solenoid valve 94 and the exhalation valve assembly 130. Thus, whenever solenoid valve 94 is open, the positive-pressure in chamber 66 is applied via tube 92 to mushroom valve 134 to close valve opening 136, and thereby to effect inhalation of the air outletted from the pump unit 2 via tubes 82, 86 and humidifier unit 4 to the delivery tube 112; and when solenoid valve 94 is closed, mushroom valve 134 opens its valve opening 136 to establish communication between delivery tube 112 and the venting ports 132 to permit exhalation to the atmosphere by the patient.

It will thus be seen that a high degree of control may be effected merely by controlling solenoid valve 94 and also by controlling the speed of rotation of motor 14. During exhalation, the motor is turned off. Both the moisture content and the temperature of the humidified air may be conveniently controlled by controlling electrical heater 120.

In emergencies, the pump unit 2 may be used alone, i.e., without the humidifier unit 4.

Whenever it is desired to withdraw fluids from the patient's lungs, the humidifier unit 4 is disconnected from the positive-pressure side of pump unit 2, and the fluid collector unit 6 is connected to the negative-pressure inlet 70. In addition, a catheter tube is applied to the inlet coupling 148 of the fluid collector unit 6, so that the negative pressure produced by the pump unit 2 is now applied to the patient's lungs via the catheter tube thereby drawing out fluid collected therein into the fluid collector unit 6.

Figure 2:
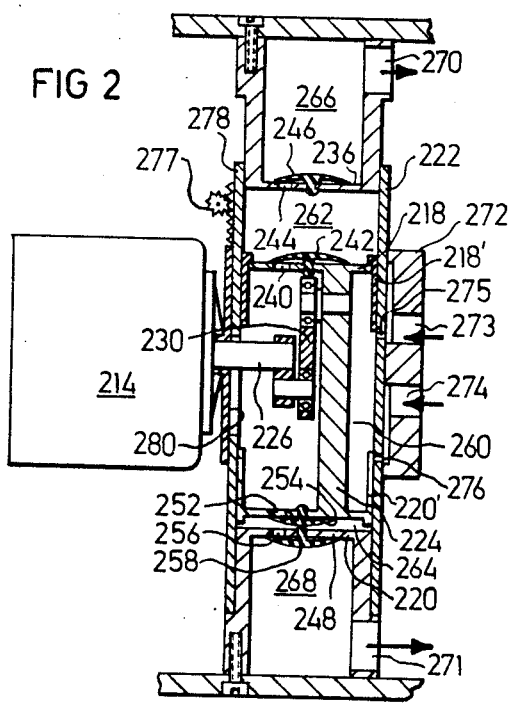
FIG. 2 illustrates the ventilator apparatus equipped with proportioning means for controlling the proportion of air and oxygen supplied to the patient.

The Variation of FIG. 2

FIG. 2 illustrates a variation wherein the pump unit may include a quantity of oxygen mixed with the air according to any desired proportion. This variation also includes a motor 214 driving a pair of pistons 218, 220 disposed within a cylinder 222 and connected together by a piston rod 224 coupled by a crank arm 230 to the output shaft 226 of the motor. The ends of cylinder 222 outwardly of pistons 218, 220, include end walls 236, 248 formed with ports 240, 244 and 252, 256, closed by umbrella-type valves 242, 246 and 254, 258, respectively, so as to define an inner negative-pressure chamber 260, and outer-positive chambers 262, 266 at one side, and 264, 268 on the opposite side, as described above with respect to FIG. 1. The positive-pressure air (or air-oxygen mixture) is outputted from chambers 266, 268 via outlet ports 270, 271.

In the arrangement illustrated in FIG. 2, the negative-pressure chamber 260 is bordered by an end wall 272 formed with two inlet ports, namely an air inlet port 273 and an oxygen inlet port 274. Cylinder 222 is also provided with two orifices, namely orifice 275 communicating with the air inlet port 273 for inletting air into the negative pressure chamber 260, and orifice 276 communicating with the oxygen inlet 274 for inletting oxygen into that chamber. In addition, cylinder 222 is adjustable by a manually-rotatable pinion 277 meshing with a rack 278 secured to cylinder 222 so as to change the relative positions of orifices 275, 276 with respect to pistons 218 and 220, particularly the skirts 218', 220' of these pistons. Cylinder 222 is formed with an elongated slot 280 at its opposite side to accommodate the motor shaft 226 during this adjustment of the cylinder.

FIG. 2 illustrates cylinder 222 preset to an adjusted position wherein piston skirt 220' always covers the oxygen inlet orifice 276 during the reciprocation of the piston assembly; accordingly, no oxygen will be included in the gas drawn into the negative-pressure chamber 260 and pumped out through the outlets 270, 271.

In order to include oxygen in the air, pinion 277 is manually rotated to move cylinder 222 (upwardly in FIG. 2), and thereby to uncover the oxygen inlet orifice 276 for at least a portion of the reciprocatory cycle of the pistons 218, 220. It will be appreciated that the proportion of oxygen to be added to the air is increased by increasing the distance cylinder 222 is adjusted in this direction, since this will increase the proportion of the reciprocatory cycle in which the oxygen inlet orifice 276 is uncovered by piston skirt 220'.

Figure 3:
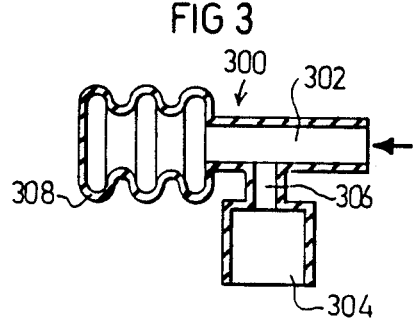
FIG. 3 is a fragmentary view illustrating the construction of the flow passageways in the ventilator apparatus of FIG. 1.

Variation of FIG. 3

FIG. 3 illustrates a variation in the construction of the flow path in order to damp the pulses generated by the reciprocating pistons. For example, the coupling illustrated in FIG. 3 could be applied between the outlet fittings 80, 84 and their outlet tubes 82, 86, and/or between the outlet coupling 110 and the delivery tube 112.

Thus, the coupling illustrated in FIG. 3, therein generally designated 300, comprises an air inlet 302 (e.g., coupled to outlet fitting 110), an air outlet 304 (e.g., coupled to the delivery tube 112), and a communicating orifice 306 between the two couplings. Inlet coupling 302 further includes an expansible, flexible bellows 308 just upstream of orifice 306, which smoothes out the air flow from the air inlet 302 to the air outlet 304.

Figure 4:
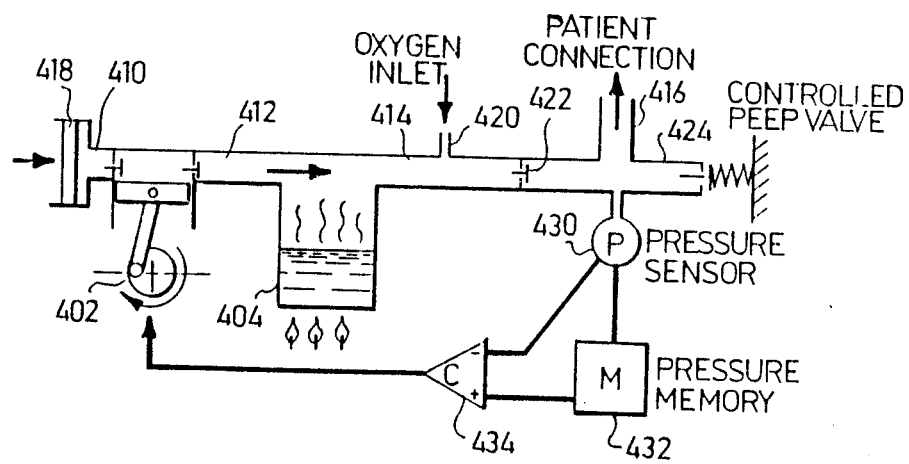
FIG. 4 schematically illustrates a modification to adapt the apparatus for operating as a CPAP (continuous positive airway pressure) ventilator.

The Embodiment of FIG. 4

FIG. 4 illustrates an embodiment of the invention particularly designed for use as a CPAP (continuous positive airway pressure) ventilator, for applying a positive pressure to a patient's lungs in order to help alleviate obstructive apnea during sleep. The illustrated apparatus comprises a pump unit schematically indicated at 402, and a heated humidifier unit schematically indicated at 404, both of which units may be of the construction as described above with respect to FIG. 1. Pump unit 402 includes a negative-pressure air inlet 410 and a positive-pressure air outlet 412 for delivering the pressurized air to the patient via a delivery conduit 414 having a connection 416 leading to the patient's mask (not shown). The pressurized air supplied to the patient via delivery conduit 414 is first passed through the heated humidifier unit 404 for heating and humidfying the air. The negative-pressure air inlet includes an air entry filter 418 for filtering the air supplied to the patient In addition, the delivery conduit 414 may include an oxygen inlet 420 for adding oxygen to the air supplied to the patient The delivery conduit 414 further includes a one-way valve 422 to permit air flow only from the pump unit 402 to the patient connection 416. The delivery tube 414 further includes a spring-control PEEP (Positive End Expiratory Pressure) valve 424, which acts as a relief valve to release the pressure within the delivery conduit 414 to the atmosphere whenever that pressure rises above a predetermined peak value.

The ventilator apparatus illustrated in FIG. 4 further includes a pressure sensor 430, a pressure memory 432, and a comparator 434 controlling the pump unit 402. Sensor 430 is an electrical sensor which senses the pressure in the delivery conduit 414 and produces an electrical output corresponding to the sensed pressure. Memory unit 432 is an electrical storage device which stores the peak pressure sensed by sensor 430. Comparator 434 is an electrical comparator circuit which compares the current pressure sensed by sensor 430 with the peak pressure stored in memory unit 432. Comparator 434 is effective to energize the pump unit 402 whenever the sensed pressure in the delivery conduit 414 is below (e.g., 5-10% below in order to introduce hysteresis into the system) the peak pressure stored in memory unit 432, and to deenergize the pump unit whenever the sensed pressure is substantially equal to or above the stored peak pressure Thus, the pump is intermittently operated, sufficiently only to maintain the peak pressure, rather than continuously operated, thereby saving power, as well as oxygen and moisture when included in the pressurized air supplied to the patient It will be appreciated that the expansible bellows may be an expansible diaphragm, and that many other variations, modifications and applications of the invention may be made within the scope of the appended claims

What is claimed is:

1. Ventilator apparatus comprising: a pump including a negative-pressure chamber having an inlet for drawing air into the chamber, and a positive-pressure chamber having an outlet for outletting pressurized air; delivery means for delivering pressurized air to a patient; an exhalation valve assembly producing breathing cycles in which the delivery means is first connected to the patient to effect inhalation, and then is vented to the atmosphere to permit exhalation; and a control valve operated by said pump for controlling the breathing cycles of the exhalation valve; characterized in that said pump is a cyclically-operated reciprocating pump and has a low volume displacement in the order of the displacement produced by a piston-type pump having a piston diameter of less than 40 mm, operates at a cyclical speed to effect at least 2 cycles of operation for each breathing cycle of the exhalation valve, and includes an expansible member in the flow path of the air from the positive pressure chamber to the delivery means to damp oscillations produced by the reciprocating pump.

2. The apparatus according to claim 1, wherein said pump includes two pistons reciprocated within a cylinder, each of said pistons having a diameter of less than 40 mm.

3. The apparatus to claim 1, further including an air inlet into said negative-pressure chamber, an oxygen inlet into said negative-pressure chamber, and proportioning means controlling the proportion of the air and oxygen inletted via their respective inlets.

4. The apparatus according to claim 3, wherein said pump comprises a pair of pistons reciprocatable in opposite ends of a cylinder; said proportioning means comprises air and oxygen orifices formed in opposite ends of said cylinder each adjacent one of the pistons, and an ajustable mounting for said cylinder with respect to said pistons such that adjusting the cylinder in one direction causes the air orifice to be uncovered a greater part of the reciprocatory cycle thereby increasing the proportion of air in the delivered gas, and adjusting the cylinder in the opposite direction causes the oxygen orifice to be uncovered a greater part of the reciprocatory cycle thereby increasing the proportion of oxygen in the delivered gas.

5. The apparatus according to claim 4, wherein said cylinder is adjustable by a pinion and rack mechanism.

6. The apparatus according to claim 1, further including a relief valve communicating with said delivery means for preventing the pressure in the delivery means from rising above a predetermined peak; a sensor for sensing the pressure in said delivery means; and control means effective to energize said pump when the sensed pressure in the delivery means is below said peak value, and to deenergize the pump when the sensed pressure is substantially equal to said peak value.

7. The apparatus according to claim 6, wherein said control means comprises a storage device for storing the peak pressure sensed by said sensor, and a comparator for continuously comparing the sensed pressure with the stored peak pressure and effective to energize the pump whenever the sensed pressure in the delivery means is below said stored peak value, and to deenergize the pump whenever the sensed pressure is substantially equal to said stored peak value.

8. The apparatus according to claim 7, wherein said pressure sensor produces an electrical output corresponding to the pressure sensed by the sensor, said storage means being an electrical device storing the peak pressure sensed by the sensor, said comparator being an electrical comparator circuit for comparing the sensed pressure with the peak pressure stored in said storage device.

9. The apparatus according to claim 6, wherein said control means is effective to energize said pump when the sensed pressure in the delivery means is 5–10% below said peak pressure.

10. The apparatus according to claim 1, wherein said pump is operated at a speed of 20 to 30 cycles per breathing cycle.

11. Ventilator apparatus comprising: a reciprocating pump including a negative-pressure chamber having an inlet for drawing air into the chamber, and a positive-pressure chamber having an outlet for outletting pressurized air; delivery means for delivering pressurized air to a patient; an exhalation valve assembly producing breathing cycles in which the delivery means is first connected to the patient to effect inhalation, and then is vented to the atmosphere to permit exhalation; control means for operating said pump at a speed to effect at least two cycles of operation for each breathing cycle of the exhalation valve; and a control valve operated by said pump for controlling the breathing cycles of the exhalation valve; said pump including an expansible bellows in the flow path of the air from the positive-pressure chamber to the delivery means to damp oscillations in pressure produced by the reciprocating pump.

12. The apparatus according to claim 11, wherein said pump has a low volume-displacement in the order of the displacement produced by a piston-type pump having a piston diameter of less than 40 mm and said control means operates the pump at 20–30 cycles of operation for each breathing cycle of the exhalation valve.

13. The apparatus according to claim 12, wherein said pump includes two pistons reciprocated within a cylinder, each of said pistons having a diameter of less than 40 mm.

14. The apparatus according to claim 11, further including an air inlet into said negative-pressure chamber, an oxygen inlet into said negative-pressure chamber, and proportioning means controlling the proportion of the air and oxygen inletted via their respective inlets.

15. The apparatus according to claim 14, wherein said pump comprises a pair of pistons reciprocatable in opposite ends of a cylinder; said proportioning means comprising air and oxygen orifices formed in opposite ends of said cylinder each adjacent one of the pistons, and an ajustable mounting for said cylinder with respect to said pistons such that adjusting the cylinder in one direction causes the air orifice to be uncovered a greater part of the reciprocatory cycle thereby increasing the proportion of air in the delivered gas, and adjusting the cylinder in the opposite direction causes the oxygen orifice to be uncovered a greater part of the reciprocatory cycle thereby increasing the proportion of oxygen in the delivered gas.

16. The apparatus according to claim 11, further including a relief valve communicating with said delivery means for preventing the pressure in the delivery means from rising above a predetermined peak; a sensor for sensing the pressure in said delivery means; and control means effective to energize said pump when the sensed pressure in the delivery means is below said peak value, and to deenergize the pump when the sensed pressure is substantially equal to said peak value.

17. Ventilator apparatus comprising: a cyclically-operated reciprocating pump including a negative-pressure chamber having an inlet for drawing air into the chamber, and a positive-pressure chamber having an outlet for outletting pressurized air; delivery means for delivering pressurized air to a patient; an exhalation valve assembly producing breathing cycles in which the delivery means is first connected to the patient to effect inhalation, and then is vented to the atmosphere to permit exhalation; a control valve operated by said pump for controlling the breathing cycles of the exhalation valve; control means for operating said pump at a speed to effect at least two cycles of operation for each breathing cycle of the exhalation valve; an air inlet into said negative-pressure chamber; an oxygen inlet into said negative-pressure chamber; and proportioning means controlling the proportion of the air and oxygen inletted via their respective inlets.

18. The apparatus according to claim 17, wherein said pump comprises a pair of pistons reciprocatable in opposite ends of a cylinder; said proportioning means comprising air and oxygen orifices formed in opposite ends of said cylinder each adjacent one of the pistons, and an ajustable mounting for said cylinder with respect to said pistons such that adjusting the cylinder in one direction causes the air orifice to be uncovered a greater part of the reciprocatory cycle thereby increasing the proportion of air in the delivered gas, and adjusting the cylinder in the opposite direction causes the oxygen orifice to be uncovered a greater part of the reciprocatory cycle thereby increasing the proportion of oxygen in the delivered gas.

19. The apparatus according to claim 17, further including a relief valve communicating with said delivery mans for preventing the pressure in the delivery means from rising above a predetermined peak; a sensor for sensing the pressure in said delivery means; and control means effective to energize said pump when the sensed pressure in the delivery means is below said peak value, and to deenergize the pump when the sensed pressure is substantially equal to said peak value.

20. The apparatus according to claim 17, wherein said pump includes an expansible member in the flow path of the air from the positive pressure chamber to the delivery means to damp oscillations produced by the reciprocating pump.

* * * * *